US011399963B2

(12) United States Patent
Huff et al.

(10) Patent No.: US 11,399,963 B2
(45) Date of Patent: Aug. 2, 2022

(54) SURGICAL INSTRUMENT AND METHOD OF POSITIONING AN ACETABULAR PROSTHETIC COMPONENT

(71) Applicant: DePuy Ireland Unlimited Company, Ringaskiddy (IE)

(72) Inventors: Daniel N. Huff, Warsaw, IN (US); Thomas S. Camino, Fort Wayne, IN (US)

(73) Assignee: DePuy Ireland Unlimited Company, Ringaskiddy (IE)

( * ) Notice: Subject to any disclaimer, the term of this patent is extended or adjusted under 35 U.S.C. 154(b) by 0 days.

(21) Appl. No.: 16/874,995

(22) Filed: May 15, 2020

(65) Prior Publication Data

US 2021/0353433 A1 Nov. 18, 2021

(51) Int. Cl.

*A61F 2/46* (2006.01)
*A61F 2/34* (2006.01)
*A61F 2/36* (2006.01)
*A61F 2/30* (2006.01)

(52) U.S. Cl.

CPC .............. *A61F 2/4609* (2013.01); *A61F 2/34* (2013.01); *A61F 2/3609* (2013.01); *A61F 2/4607* (2013.01); *A61F 2/4684* (2013.01); *A61F 2002/30593* (2013.01); *A61F 2002/30845* (2013.01)

(58) Field of Classification Search

CPC .. A61B 2017/00455; A61B 2017/0046; A61B 2017/00477; A61F 2/4607; A61F 2/4684

See application file for complete search history.

(56) References Cited

U.S. PATENT DOCUMENTS 4,517,969 A 5/1985 Halcomb, III et al.
5,569,263 A * 10/1996 Hein .................. A61B 17/1659 606/102
5,766,261 A 6/1998 Neal et al.
5,885,295 A 3/1999 McDaniel et al.
6,179,877 B1 1/2001 Burke (Continued)

FOREIGN PATENT DOCUMENTS

CA 2714712 A1 9/2009
EP 2605727 A2 6/2013

(Continued)

*Primary Examiner* — Anu Ramana
(74) *Attorney, Agent, or Firm* — Barnes & Thornburg LLP

(57) ABSTRACT

A system for use during an orthopaedic surgical procedure includes a femoral broach, an acetabular cup component, and an acetabular alignment guide. The femoral broach includes a mounting post positioned at a superior end of an elongated body. The cup component includes a distal rim and a curved surface extending inwardly from the rim to define a cavity. The alignment guide includes a distal end configured to be coupled to the mounting post and a proximal end configured to be coupled to the distal rim. When coupled to the femoral broach, the guide instrument is sized to orient the acetabular cup component relative to the femoral broach. The acetabular cup component may be a prosthetic cup component or a trial instrument corresponding to the prosthetic cup component.

13 Claims, 8 Drawing Sheets

166
168
102
α
γ
162
170
FIG.5
106
θ
130
104
124
110
108
112

(56) References Cited

U.S. PATENT DOCUMENTS

| | | | | |
|---|---|---|---|---|
| 7,445,638 | B2 * | 11/2008 | Beguin | A61F 2/4014 623/19.12 |
| 7,608,112 | B1 | 10/2009 | Kuczynski et al. | |
| 7,828,806 | B2 | 11/2010 | Graf et al. | |
| 8,361,162 | B2 | 1/2013 | Berry et al. | |
| 8,603,180 | B2 | 12/2013 | White et al. | |
| 9,155,632 | B2 | 10/2015 | Termanini | |
| 9,326,862 | B2 | 5/2016 | Smith et al. | |
| 9,615,942 | B2 * | 4/2017 | Smith | A61F 2/468 |
| 10,524,933 | B2 * | 1/2020 | Moore | A61B 90/06 |
| 2004/0015238 | A1 | 1/2004 | Buehler et al. | |
| 2006/0058886 | A1 | 3/2006 | Wozencroft | |
| 2012/0265319 | A1 | 10/2012 | Prybyla et al. | |

FOREIGN PATENT DOCUMENTS

| | | | | |
|---|---|---|---|---|
| WO | 2009106813 | A1 | 9/2009 | |
| WO | 2012024288 | A2 | 2/2012 | |
| WO | 2012048362 | A1 | 4/2012 | |
| WO | 2012158917 | A1 | 11/2012 | |
| WO | 2013153401 | A1 | 10/2013 | |
| WO | WO-2019068430 | A1 * | 4/2019 | A61F 2/4684 |

* cited by examiner

SURGICAL INSTRUMENT AND METHOD OF POSITIONING AN ACETABULAR PROSTHETIC COMPONENT

TECHNICAL FIELD

The present disclosure relates generally to orthopaedic surgical instruments and, more particularly, to surgical instruments used to trial and install an acetabular prosthetic component.

BACKGROUND

Joint arthroplasty is a well-known surgical procedure by which a diseased and/or damaged natural joint is replaced by a prosthetic joint. For example, in a hip arthroplasty surgical procedure, a patient's natural hip ball and socket joint is partially or totally replaced by a prosthetic hip joint. A typical prosthetic hip joint includes an acetabular prosthetic component and a femoral head prosthetic component. An acetabular prosthetic component generally includes an outer shell configured to engage the acetabulum of the patient and an inner bearing or liner coupled to the shell and configured to engage the femoral head. The femoral head prosthetic component and inner liner of the acetabular component form a ball and socket joint that approximates the natural hip joint.

To facilitate the replacement of the natural joint with a prosthetic hip joint, orthopaedic surgeons may use a variety of orthopaedic surgical instruments such as, for example, reamers, drill guides, drills, positioners, and/or other surgical instruments.

SUMMARY

According to one aspect of the disclosure, a system for use during an orthopaedic surgical procedure includes a femoral component and an acetabular alignment guide instrument. The femoral component includes an elongated body extending along a longitudinal axis from a superior end to an inferior tip. The superior end of the elongated body includes a planar outer surface. The femoral component further includes a post extending superiorly from the planar outer surface of the elongated body. The acetabular alignment guide instrument includes a distal end configured to be coupled to the post of the femoral component and a proximal engagement rim configured to be coupled to an acetabular cup component. While the acetabular alignment guide instrument is coupled to the femoral component, the planar outer surface of the elongated body of the femoral component defines a first imaginary plane, and the proximal engagement rim of the alignment guide instrument defines a second imaginary plane that is not parallel to the first imaginary plane.

In an embodiment, a first angle is defined between the first imaginary plane and the second imaginary plane when the acetabular alignment guide instrument and the femoral component are viewed in a first visual plane. A second angle is defined between the first imaginary plane and the second imaginary plane when the acetabular alignment guide instrument and the femoral component are viewed in a second visual plane extending orthogonal to the first visual plane. The first angle or the second angle is nonzero. In an embodiment, the system further includes an acetabular cup component including a rim surface and a concave curved inner surface, the concave curved inner surface extending inwardly from the rim surface to define a cavity sized to receive a femoral head component. Each of the first angle and the second angle has a magnitude, and when the guide instrument is coupled to the acetabular cup component, the magnitudes of the first angle and the second angle orient the acetabular cup component insertion into a patient's acetabulum at a predetermined anteversion angle and a predetermined abduction angle. In an embodiment, the guide instrument further includes an adjustment mechanism operable to change a magnitude of at least one of the first angle and the second angle.

In an embodiment the proximal engagement rim of the guide instrument is configured to engage a rim of the acetabular cup component. In an embodiment, the guide instrument includes a stem including the distal end of the guide instrument and a connector flange coupled to the stem, the connector flange including the proximal engagement rim of the guide instrument. In an embodiment, the proximal engagement rim includes a planar proximal rim surface, and the connector flange includes a curved inner surface that extends inwardly from the planar rim surface to define a proximal chamber in the guide instrument. In an embodiment, the stem includes a passageway that extends inwardly from the distal end of the guide instrument and opens into the proximal chamber of the guide instrument, the passageway being sized to receive the post of the femoral component.

In an embodiment, the femoral component includes a femoral broach including a plurality of cutting teeth defined along an outer surface of the elongated body.

According to another aspect, a system for use during an orthopaedic surgical procedure includes a femoral component, an acetabular cup component, and an acetabular alignment guide instrument. The femoral component includes an elongated body extending along a longitudinal axis from a superior end to an inferior tip. The superior end of the elongated body includes a planar outer surface. The femoral component further includes a post extending superiorly from the planar outer surface of the elongated body. The acetabular cup component includes a rim having a rim surface and a concave curved inner surface, the concave curved inner surface extending inwardly from the rim surface to define a cavity sized to receive a femoral head component. The acetabular alignment guide instrument includes a distal end configured to be coupled to the post of the femoral component and a proximal end configured to be coupled to the rim of the acetabular cup component. While the guide instrument is coupled to the femoral component and the acetabular cup component, the guide instrument is sized to orient the acetabular cup component relative to the femoral component such that a first angle is defined between a first imaginary plane extending along the planar outer surface of the elongated body of the femoral component and a second imaginary plane extending along the rim surface of the acetabular cup component when the guide instrument, the femoral component, and the acetabular cup component are viewed in a first visual plane, and a second angle is defined between the first imaginary and the second imaginary plane when the guide instrument, the femoral component, and the acetabular cup component are viewed in a second visual plane. The second visual plane extends orthogonal to the first visual plane, and the first angle or the second angle are nonzero.

In an embodiment, the guide instrument includes a stem including the distal end of the guide instrument and a connector flange coupled to the stem, the connector flange including the proximal end of the guide instrument and being configured to engage the rim of the acetabular cup component. In an embodiment, the connector flange includes an engagement surface configured to engage the inner surface of the acetabular cup component. In an embodiment, the engagement surface is a planar rim surface, and the connector flange includes a curved inner surface that extends inwardly from the planar rim surface to define a proximal chamber in the guide instrument. In an embodiment, the stem of the guide instrument is sized to be positioned over the post.

In an embodiment, the guide instrument further includes an adjustment mechanism operable to change a magnitude of at least one of the first angle and the second angle. In an embodiment, the acetabular cup component is at least one of an acetabular prosthetic cup component and an acetabular cup trial instrument corresponding to the acetabular prosthetic cup component.

BRIEF DESCRIPTION OF THE DRAWINGS

The detailed description particularly refers to the following figures, in which.

DETAILED DESCRIPTION OF THE DRAWINGS

Figure 1:
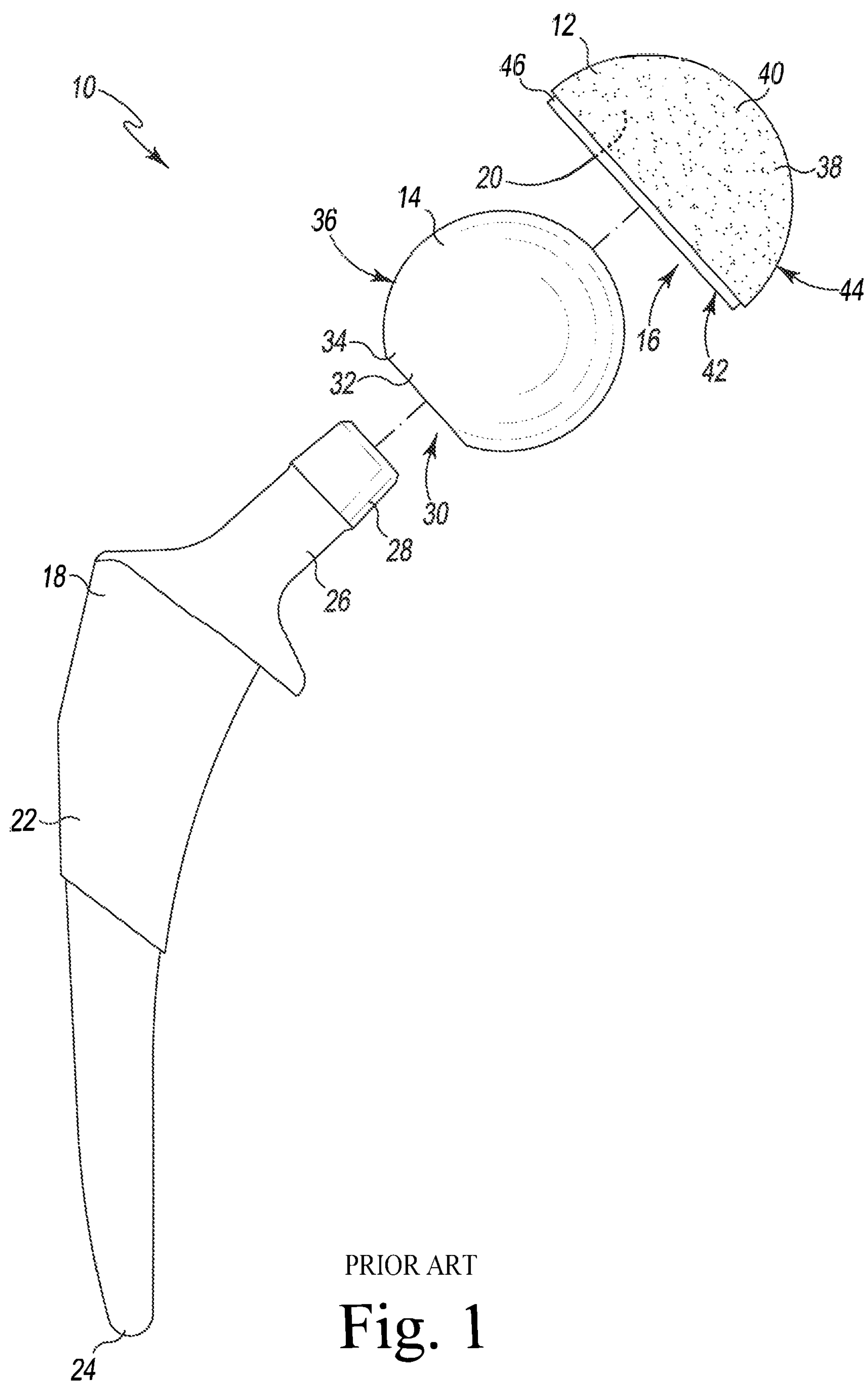
FIG. 1 is an exploded elevation view of a hip orthopaedic prosthesis assembly.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, an illustrative hip orthopaedic prosthesis assembly 10 includes several components, including an acetabular prosthesis 12 that is shaped to be implanted in a surgically-prepared acetabulum of a patient's pelvis. The assembly 10 also includes a femoral head component 14 that is received in a cavity 16 defined in the acetabular prosthesis 12. The prosthesis assembly 10 also includes a femoral stem component 18 that is configured to be secured to the femoral head component 14 to form a femoral prosthetic component. The acetabular prosthesis 12 further includes an insert component 20 that is shaped to support and stabilize the femoral head 14 over the range of motion of the prosthesis assembly 10.

In the illustrative embodiment, the femoral stem component 18 includes an elongated body 22 that extends from a distal tip 24. The stem component 18 is sized and shaped to be implanted in a surgically-prepared proximal end of a patient's femur. The stem component 18 also includes a neck 26 that extends superiorly and immediately from the elongated body 22 to a tapered trunnion 28. The tapered trunnion 28 is sized to be positioned in a distal bore 30 defined in the femoral head component 14. The bore 30 is defined by a tapered inner surface 32 that is configured to engage the tapered trunnion 28 to secure the head component 14 to the stem component 18. The femoral head component 14 and the femoral stem component 18 are separately formed from implant-grade metallic materials such as, for example, cobalt chromium.

The bore 30 of the femoral head component 14 is defined in a distal surface 34. The head component 14 also includes a convex curved surface 36 that is connected to, and extends from, the distal surface 34. In the illustrative embodiment, the convex curved surface 36 is a semi-spherical surface that is shaped to be received in the cavity 16 of the acetabular prosthesis 12.

As described above, the acetabular prosthesis 12 includes a shell liner component 20, which is configured to be coupled to a shell component 38 of the acetabular prosthesis 12. The shell liner component 20 is illustratively formed from a polymeric material such as, for example, polyethylene. The shell component 38, is separately formed from implant-grade metallic materials such as, for example, cobalt chromium. The shell component 38 also includes a Porocoat® outer coating 40 that permits bone to affix biologically to the shell component 38 after implantation. It should be appreciated that in other embodiments the Porocoat® outer coating may be omitted.

The shell component 38 has a distal rim 42 and an outer wall 44 that extends from the distal rim 42. The outer wall 44 includes a convex curved outer surface and an annular outer surface 46 that extends from the distal rim 42 to the curved outer surface. In the illustrative embodiment, the convex curved outer surface is semi-spherical and shaped to match the shape of a patient's surgical prepared acetabulum. The Porocoat® outer coating 40 covers the outer surface and follows its geometric shape.

Referring now to FIGS. 2-5, a hip orthopaedic surgical instrument assembly 100 includes a plurality of components, including an acetabular cup component 102, a femoral component 104, and an alignment guide instrument 106. The assembly 100 may be used during a hip arthroplasty surgical procedure to trial and install the femoral stem component 18 and the acetabular prosthetic component 12 in a patient's bone. As described in more detail below, in use, the femoral component 104 is inserted into a patient's surgically prepared femur. The alignment guide instrument 106 is attached to the femoral component 104, and the acetabular cup component 102 is attached to the alignment guide instrument 106. After connecting the components of the assembly 100, the acetabular cup component 102 is advanced into the patient's surgically prepared acetabulum, and the surgeon arranges the assembly 100 (including the cup component 102, the femoral broach 104, and the alignment guide instrument 106) to achieve a desired position and orientation of the patient's femur relative to the acetabulum. The alignment guide instrument 106 may be configured to position the femoral broach 104 and the cup component 102 to achieve a desired inclination, abduction, anteversion, and/or flexion angle.

It should be appreciated that, although the assembly 100 is described below in regard to the performance of a hip arthroplasty surgical procedure, certain concepts associated with the assembly 100 may be utilized in replacement procedures of numerous other joints throughout the body. In other words, one or more of the elements of the assembly 100 may be incorporated into surgical instruments used in, for example, knee, spinal, shoulder, or other replacement procedures.

Figure 2:
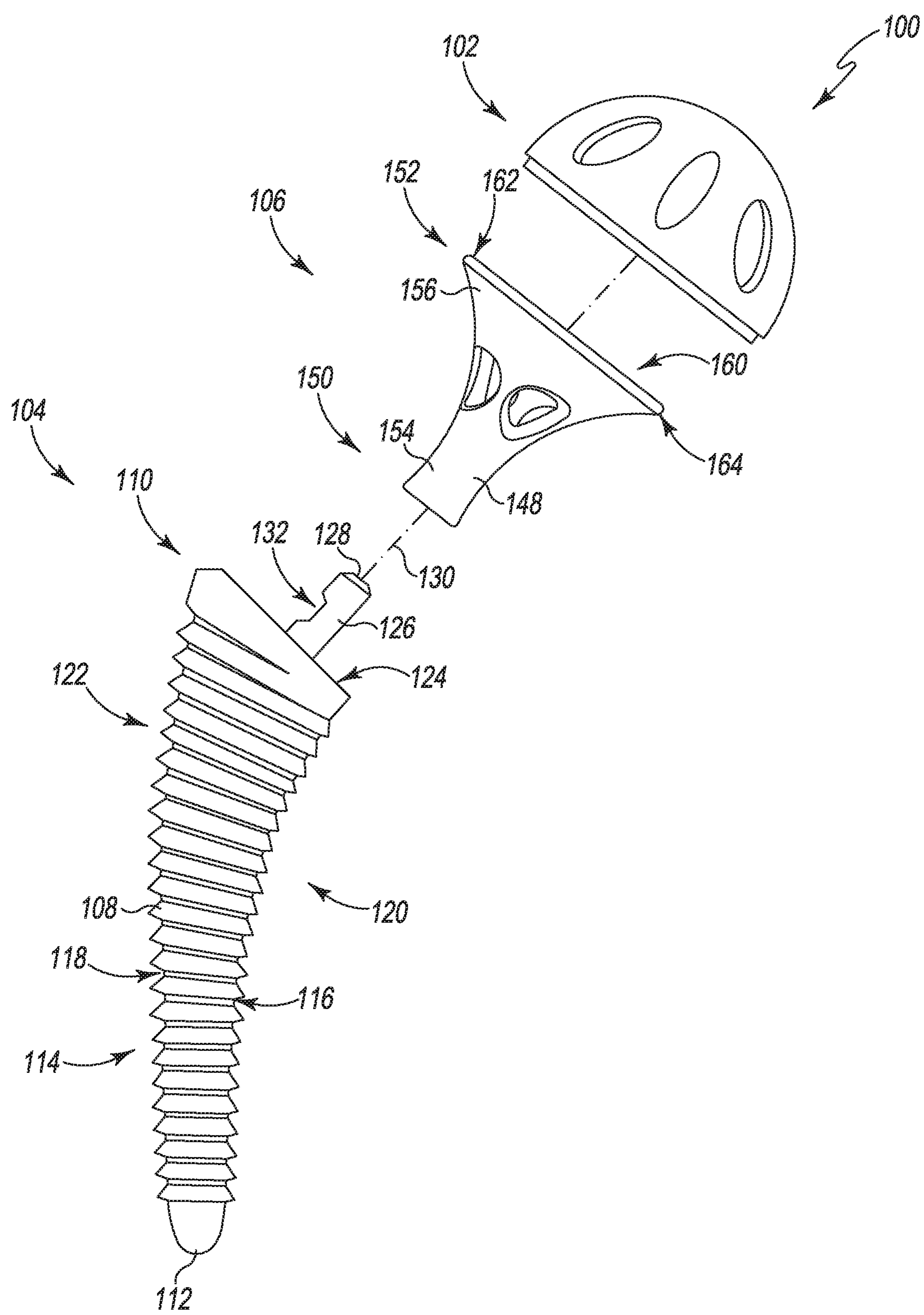
FIG. 2 is an exploded elevation view of a hip orthopaedic surgical instrument assembly.

In the illustrative embodiment, the femoral component 104 is embodied as a femoral broach. The femoral broach 104 includes an elongated body 108 that extends from a proximal end 110 to a distal tip 112. A plurality of cutting teeth 114 are defined along the length of the body 108, and each tooth 114 is shaped and sized to surgically-prepare a femoral canal of the patient's femur to receive the femoral stem component 18. When the femoral broach 104 is viewed in a coronal plane as shown in FIG. 2, the body 108 has a medial side 116 that extends from the proximal end 110 to the distal tip 112 and a lateral side 118 that is positioned opposite the medial side 116. The medial side 116 has a concave section 120 that is positioned adjacent to the proximal end 110 of the body 108, and the lateral side 118 has a corresponding convex section 122 that is positioned opposite the concave section 120. The curvatures of the sections 120, 122 correspond to the curvatures of the corresponding regions of the femoral stem component 18.

The femoral broach 104 includes a planar proximal surface 124 at the proximal end 110 of the elongated body 108. The broach 104 includes a proximal post 126 that extends outwardly from the surface 124 to a tip 128. In the illustrative embodiment, the post 126 extends along a longitudinal axis 130, which extends orthogonal to the planar surface 124. The post 126 further defines a slot 132 which may be used to secure the alignment guide instrument 106, the femoral head component 14, or another instrument to the post 126.

In the illustrative embodiment, the femoral broach 104 is formed as a single monolithic component from a metallic material such as stainless steel. It should also be appreciated that in other embodiments other materials may be used. For example, portions of the post 126 and/or elongated body 108 may be formed from a polymeric material such as polyethylene, while the edges of the cutting teeth 114 are formed from a metallic material.

Figure 3:
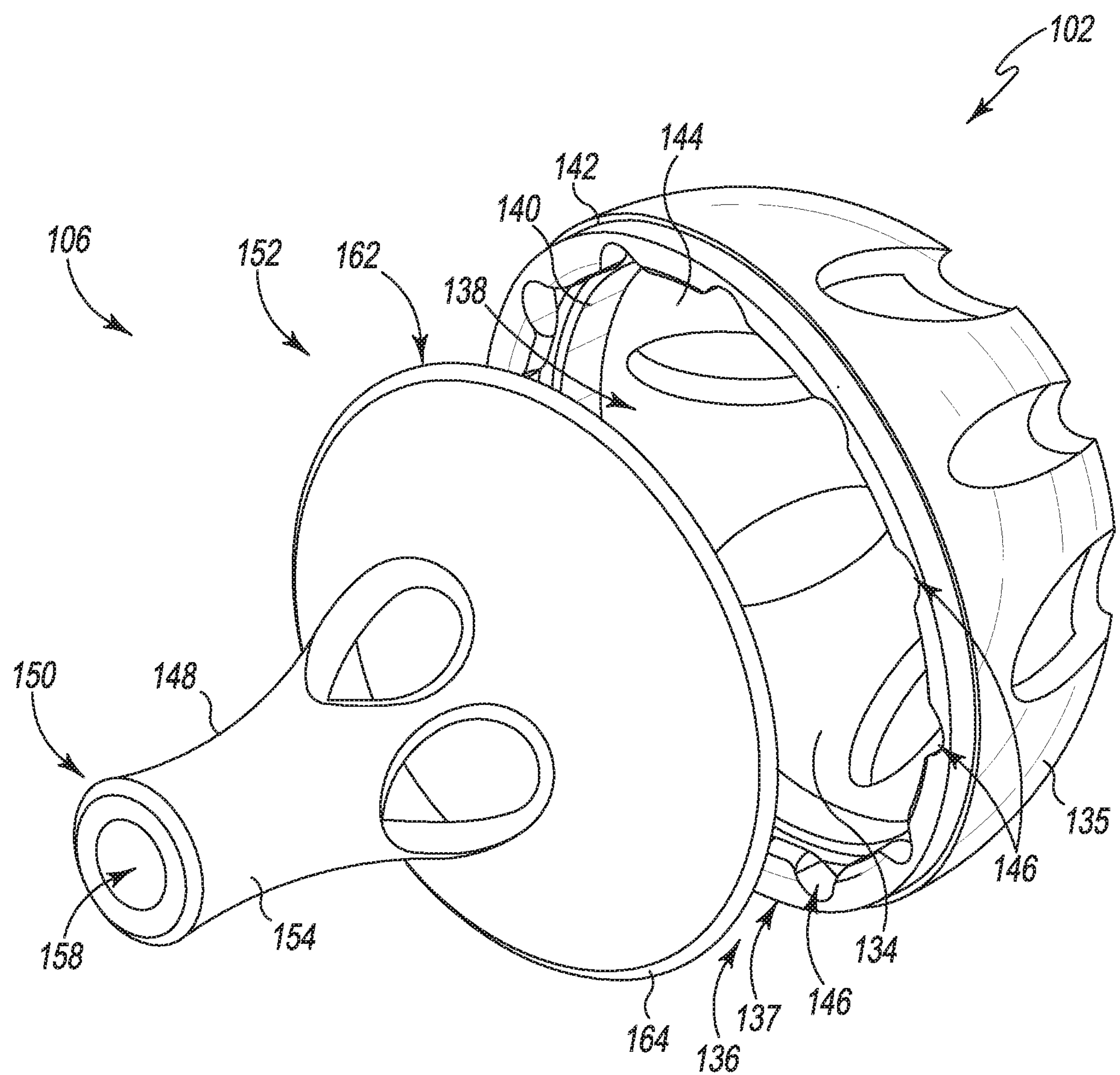
FIG. 3 is a perspective view of an alignment guide instrument and an acetabular cup component of the surgical instrument assembly of FIG. 2.

As described above, FIGS. 2-5 show the acetabular cup component 102. In the illustrative embodiment, the acetabular cup component 102 is embodied as a trial component for the acetabular prosthesis 12. In other embodiments, however, the acetabular cup component may be an implant, similar to the acetabular prosthesis 12 of FIG. 1. As best shown in FIG. 3, the illustrative cup component 102 includes a distal rim 136 that includes an inner wall 134 that extends inwardly from the distal rim 136 to define a cavity 138 in the cup component 102, and an outer wall 135 that extends outwardly from the distal rim 136 and opposite the inner wall 134. A planar distal rim surface 137 is defined between the inner wall 134 and the outer wall 135. In some embodiments, the cavity 138 may be sized to receive a shell liner component, similar to the shell liner component 20 of FIG. 1. The inner wall 134 of the distal rim 136 includes an annular inner surface 140 that is positioned opposite an annular outer surface 142, and a concave curved inner surface 144 that is connected to the annular inner surface 140. A plurality of slots 146 extend inwardly from the inner wall 134 of the distal rim 136. The slots 146 are spaced apart around the circumference of the distal rim 136 and are shaped to receive corresponding keys of the alignment guide instrument 106 to restrict rotation of the alignment guide instrument 106 relative to the acetabular cup component 102 as described in greater detail below. In some embodiments, the slots 146 may also be shaped to receive corresponding keys of a shell liner component or other prosthetic component.

The alignment guide instrument 106 includes a unitary body 148 that extends from a distal end 150 to a proximal end 152. Illustratively, the body 148 is formed from injection-molded plastic; however, in other embodiments the body 148 may be formed from any appropriate rigid material, such as a metallic material. The distal end 150 is configured to connect to the post 126 of the femoral broach 104, and the proximal end 152 is configured to connect to the distal rim 136 of the cup component 102. The body 148 has a length l defined from the distal end 150 to the proximal end 152. In use, and as described further below, when coupled together with the cup component 102 and the broach 104, the alignment guide instrument 106 rigidly supports the cup component 102 in a predetermined position and orientation relative to the femoral broach 104.

The body 148 includes a stem 154 located at the distal end 150 and a connector flange 156 located at the proximal end 152. The stem 154 defines a passageway 158 that extends through the body 148 and opens into a proximal chamber 160 of the alignment guide instrument 106. The passageway 158 is sized to be positioned over the post 126 of the femoral broach 104. In some embodiments, the passageway 158 may establish a friction fit on the post 126 sufficient to provide rotational stability. In some embodiments, the stem 154 may include one or more annular tabs extending into the passageway 158 (not shown) that engage the slot 132 of the post 126 to secure the alignment guide instrument 106 to the post 126.

The connector flange 156 includes a planar rim 162 configured to engage the cup component 102. Illustratively, the planar rim 162 includes an outer circumference 164. The outer circumference 164 is sized to be received within the annular inner surface 140 of the cup component 102. The outer circumference 164 may establish a friction fit with the annular inner surface 140. In some embodiments, the connector flange 156 may further include multiple keys (not shown) that extend outwardly from the outer circumference 164 and are positioned around the outer circumference 164 of the planar rim 162. The keys may be received by the slots 146 of the cup component 102. When the alignment guide instrument 106 and the cup component 102 are connected, the planar rim 162 of the alignment guide instrument 106 and the distal rim 136 of the cup component 102 are coplanar or otherwise parallel.

Figure 4:
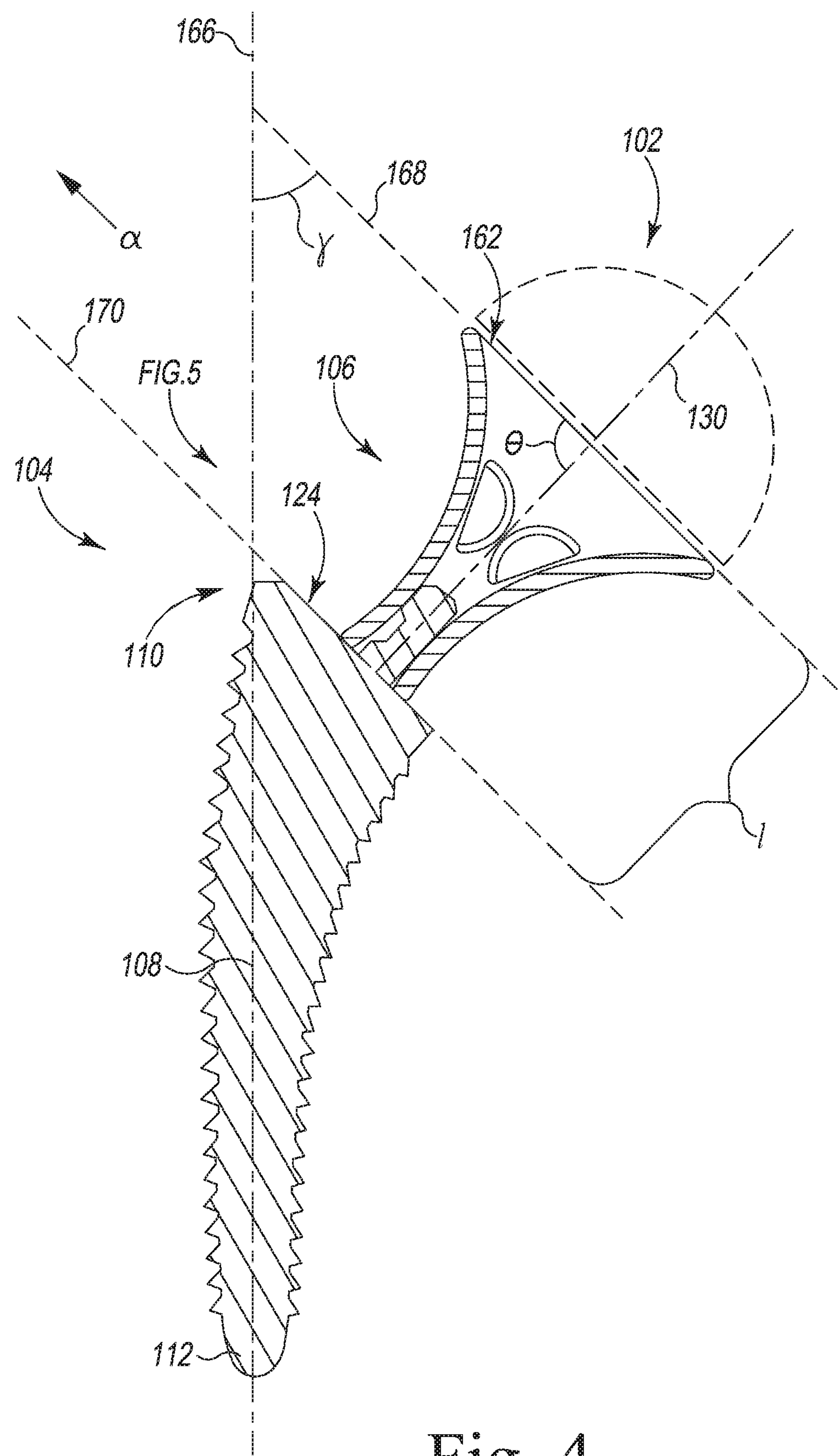
FIG. 4 is a cross-sectional view of the surgical instrument assembly of FIGS. 2-3.

Referring now to FIG. 4, the alignment guide instrument 106 is shown connected to the femoral broach 104 viewed in a coronal visual plane, similar to the exploded view of FIG. 2. As described above, the alignment guide instrument 106 may also be connected to the cup component 102, shown in phantom in FIG. 4.

As shown, the alignment guide instrument 106 defines an imaginary plane 168 that extends along the planar rim 162 at the proximal end 152. Similarly, the femoral broach 104 defines an imaginary plane 170 that extends along the planar proximal surface 124 at the superior end 110. While the broach 104 and the alignment guide instrument 106 are connected, an angle α is defined between the planes 168, 170 when viewed in the visual plane of FIG. 4. The angle α may be zero or nonzero, depending on whether the planes 168, 170 are parallel when viewed in the visual plane of FIG. 4.

A longitudinal axis 166 extends through the femoral broach 104 from the inferior tip 112 to the superior end 110. As shown, the imaginary plane 168 intersects with the longitudinal axis 166. While the broach 104 and the alignment guide instrument 106 are connected, the longitudinal axis 166 and the plane 168 define an angle γ when viewed in the visual plane of FIG. 4.

As described above, the longitudinal axis 130 extends through the post 126 orthogonal to the planar surface 124 (and thus also orthogonal to the plane 170). As shown in FIG. 4, while the broach 104 and the alignment guide instrument 106 are connected, the axis 130 intersects with the plane 168. The axis 130 and the plane 168 define an angle θ when viewed in the visual plane of FIG. 4. The planes 168, 170 are separated by the length l along the axis 130. Thus, when the alignment guide instrument 106 is seated on the post 126, at least part of the rim 162 is separated by the length l from the planar surface 124 of the femoral broach 104.

Figure 5:
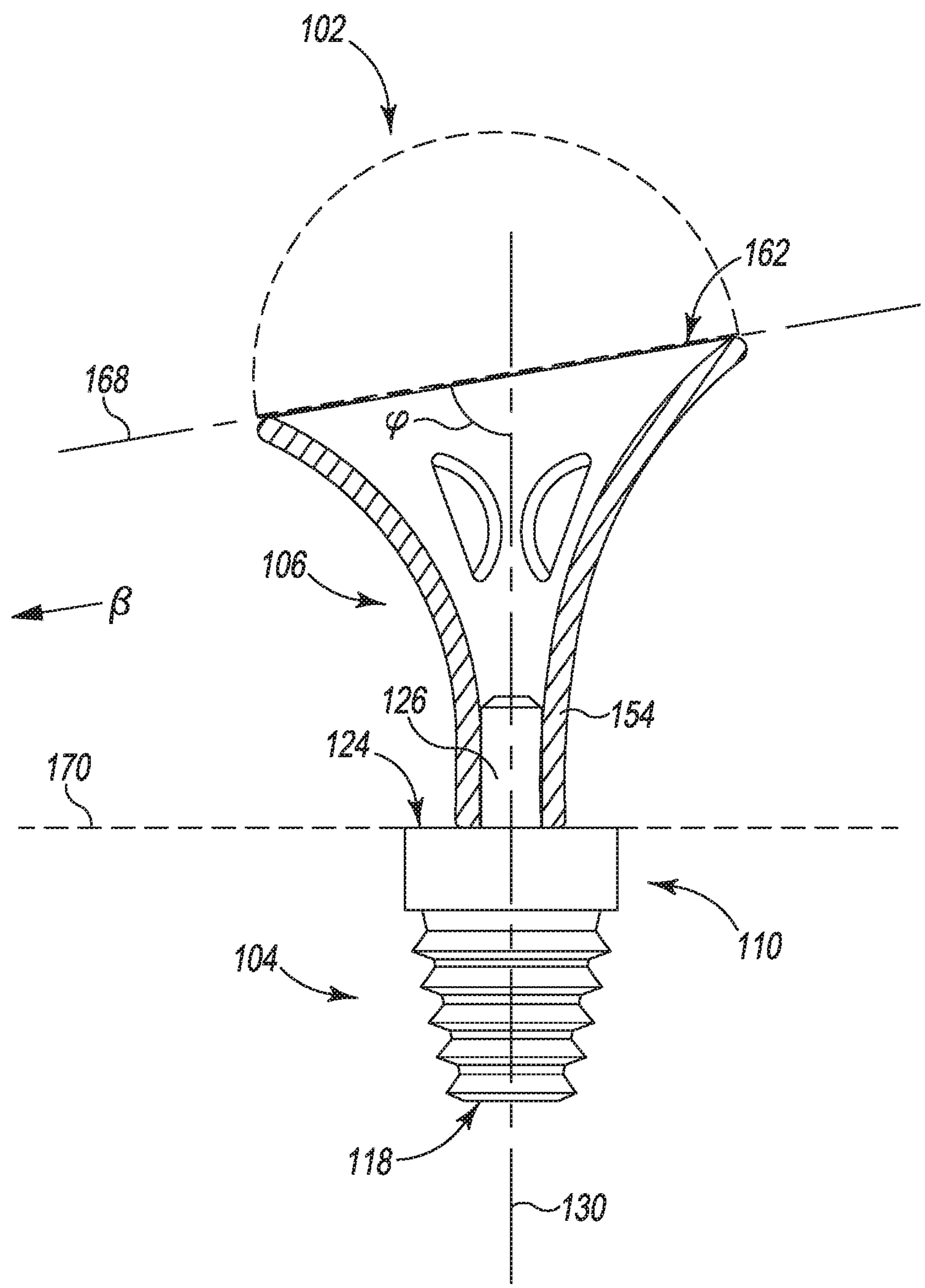
FIG. 5 is a partial cross-sectional view of the surgical instrument of FIGS. 2-4.

Referring now to FIG. 5, another view of the alignment guide instrument 106 connected to the femoral broach 104 is shown. FIG. 5 shows the femoral broach 104 and the alignment guide instrument 106 viewed along the planar surface 124 of the femoral broach 104, in a plane orthogonal to the viewing plane of FIG. 4. As described above, the alignment guide instrument 106 may also be connected to the cup component 102, shown in phantom.

As described above, the alignment guide instrument 106 defines the imaginary plane 168 that extends along the planar rim 162, and the femoral broach 104 defines the imaginary plane 170 that extends along the planar proximal surface 124. As shown in FIG. 5, when the broach 104 and the alignment guide instrument 106 are connected, an angle β is defined between the planes 168, 170 when viewed in the visual plane of FIG. 5. The angle β may be zero or nonzero depending on whether the planes 168, 170 are parallel when viewed in the visual plane of FIG. 5. In some embodiments, either one or both of the angles α, β are nonzero; in other words, in those embodiments the planes 168, 170 intersect and are thus not parallel.

Also as described above, the longitudinal axis 130 extends through the post 126 orthogonal to the planar surface 124 and intersects with the plane 168. An angle φ is defined between the axis 130 and the plane 168 when viewed in the visual plane of FIG. 5. As described above, in some embodiments, the planes 168, 170 intersect. In those embodiments, one or both of the angles θ, φ are not a right angle (i.e., have a magnitude other than 90 degrees).

In use, a surgeon or other user may utilize the alignment guide instrument 106 to trial and install a prosthetic hip joint. To do so, the surgeon prepares the patient's femur to receive a femoral stem component 18. During the surgical procedure, a surgeon or other member of the surgical team may resect the patient's femur to remove the natural femoral head and create a substantially planar proximal surface on the patient's femur. The surgeon may use an osteotome to create an opening into the femoral canal.

The surgeon may then insert the femoral broach 104 through the opening into the femoral canal and advance the broach 104 distally along the canal to size and shape the canal to receive the femoral stem component 18. If the surgeon determines that the femoral broach 104 is not axially and rotationally stable when seated in the canal, the surgeon may withdraw the first broach 104 from femoral canal, select another broach 104 that is larger in size, and insert that broach 104 into the canal. The surgeon may continue to increase broach sizes until the selected broach 104 attains axial and rotational stability and is seated at a level that recreates proper leg length for the patient. With the broach 104 seated in the femoral canal, the surgeon may further surgically prepare the patient's femur by connecting one or more surgical instruments to the post 126 of the broach 104. For example, the surgeon may resect the medial calcar of the patient's femur with a reamer or other surgical instrument.

The surgeon also surgically prepares the patient's natural acetabulum to receive an acetabular prosthesis 12. To do so, the surgeon may utilize a surgical reamer to prepare the patient's bone to receive the prosthesis 12. After preparing the patient's femur and acetabulum, the surgeon may then perform a trial reduction with the broach 104 seated in the femoral canal, assessing, for example, component position, joint stability, range of motion, and leg length.

With the femoral broach 104 seated in the femoral canal, the surgeon slides the alignment guide instrument 106 onto the post 126 until the distal end 150 contacts the planar surface 124. The surgeon may ensure that the alignment guide instrument 106 is located on the post 126 in a predetermined rotational orientation. For example, the surgeon may ensure that the alignment guide instrument 106 engages the slot 132 of the post 126. As another example, the surgeon may determine the rotational orientation of the guide instrument 106 based on markings or other indications on the alignment guide instrument 106. As described above, when connected to the femoral broach 104, the rigid body 148 of the alignment guide instrument 106 supports the planar rim 162 of the alignment guide instrument 106 in a predetermined position and orientation relative to the femoral broach 104. The position and orientation of the planar rim 162 are determined by the combination of the angles α, β and the length l (or, alternatively, the angles θ, φ and the length l, the angles γ, φ and the length l, and/or another combination of angles and length).

The surgeon connects the acetabular cup component 102 to the proximal end 152 of the alignment guide instrument 106, thereby assembling the surgical instrument assembly 100. When so assembled, the alignment guide instrument 106 supports the acetabular cup component 102 in a predetermined position and orientation relative to the femoral broach 104 that is determined by the combination of the angles α, β and the length l (or, alternatively, the angles θ, φ and the length l, the angles γ, φ and the length l, and/or another combination of angles and length).

Figure 6:
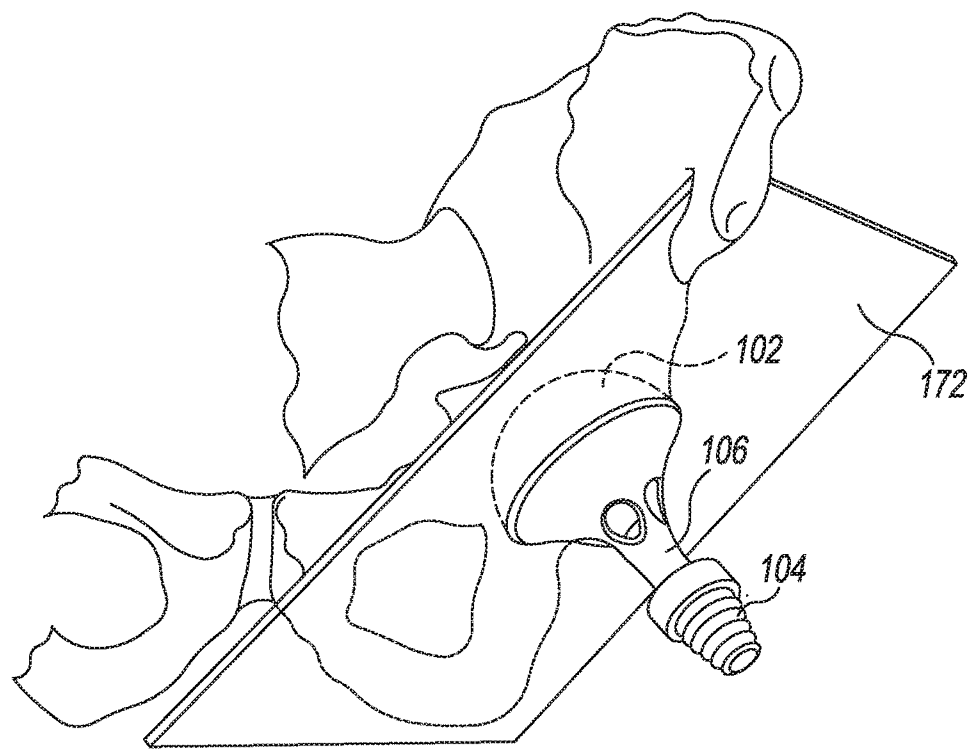
FIG. 6 is a perspective view of the orthopaedic surgical instrument assembly of FIGS. 2-5 in a reference position.
Figure 7:
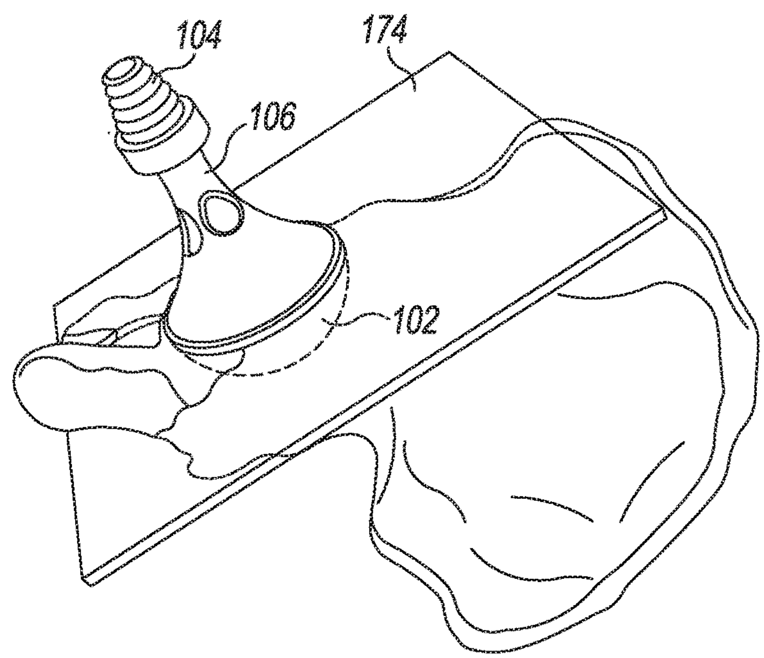
FIG. 7 is another perspective view of the orthopaedic surgical instrument assembly of FIGS. 2-6 in the reference position of FIG. 6.

With the acetabular cup component 102 secured to the alignment guide instrument 106, the acetabular cup component 102 is advanced into the patient's surgically prepared acetabulum (see FIGS. 6-7). With the cup component 102 inserted into the patient's acetabulum, the surgeon arranges the assembly 100 (including the cup component 102, the femoral broach 104, and the alignment guide instrument 106) to achieve a desired position and orientation of the patient's femur relative to the acetabulum, for example based on a desired inclination, abduction, anteversion, and/or flexion angle. After positioning the acetabular cup component 102 in the desired position and orientation, the surgeon installs the acetabular prosthesis 12.

In the illustrative embodiment, the acetabular cup component 102 is a trial component for the acetabular prosthesis 12. With a trial component 102, the surgeon may use the assembly 100 to determine the type, configuration, and installed position of the acetabular prosthetic component 12 that is to be implanted. For example, the surgeon may use the cup component 102 to scribe or otherwise mark the patient's acetabulum for impaction of the final acetabular prosthesis 12. Alternatively, in some embodiments the acetabular cup component 102 may be the final acetabular prosthesis 12 that is fixed in the desired position and orientation.

The surgeon may select the angles α, β and/or length l of the alignment guide instrument 106 in order to achieve a desired combined version angle, abduction angle, and/or flexion angle for all components of the prosthetic hip joint. For example, referring now to FIG. 6, appropriate magnitudes for the angles α, β may be selected to achieve a predetermined inclination angle 172. The inclination angle 172 may be between 40° and 45°. As another example, referring now to FIG. 7, appropriate magnitudes for the angles α, β may be selected to achieve a predetermined version angle 174. The version angle 174 may be between 15° and 20°. The desired inclination and/or version angles may be patient-specific or otherwise determined by the surgeon. To achieve the desired angles, the surgeon may select from multiple alignment guide instruments 106 that each have different angles α, β and/or lengths l in order to achieve the desired combination of version, inclination, varus/valgus, and/or flexion. Additionally or alternatively, in some embodiments a customized, patient-specific alignment guide instrument 106 (i.e., a structure that has been created for use with a single patient) may be used. Additionally, although described in terms of the angles α, β, it should be understood that in some embodiments the surgeon may select the alignment guide instrument 106 based on the angles θ, φ, the angles γ, φ, or another appropriate combination of angles.

Thus, by positioning the acetabular cup component 102 using the instrument assembly 100, the surgeon may account for combined angles creating the kinematic relationships of components across the prosthetic hip joint. Accordingly, positioning the acetabular cup component 102 using the instrument assembly 100 may achieve improved positioning relative to alignment guides or jigs that are based on landmarks of the acetabulum or those that are based on an assumed plane relative to the surgical table. For example, an acetabular cup component 12 positioned vertically in the acetabulum may have no fixation or performance problems on its own, but being vertical in relation to the femoral component 18 and abductor load forces may cause rim loading and edge wear. The instrument assembly 100 allows combined version across the prosthesis system 10 to be considered. Thus, cup loading may become more consistent, because the cup component 12 is placed relative to the broach 104, and the broach 104 has a relatively consistent positional relationship to the greater trochanter where the abductors attach.

Figure 8:
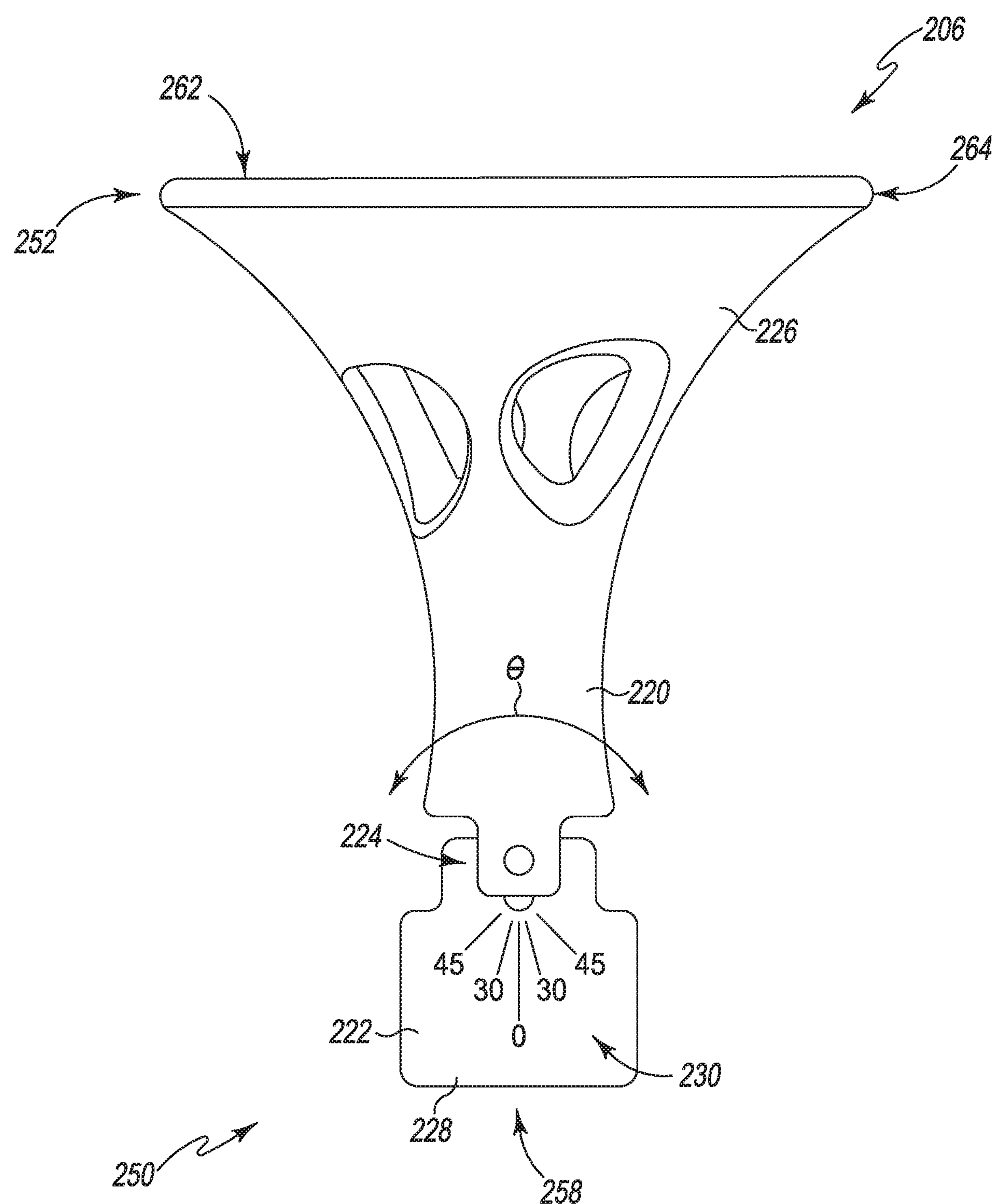
FIG. 8 is a side view of another embodiment of an alignment guide instrument.
Figure 9:
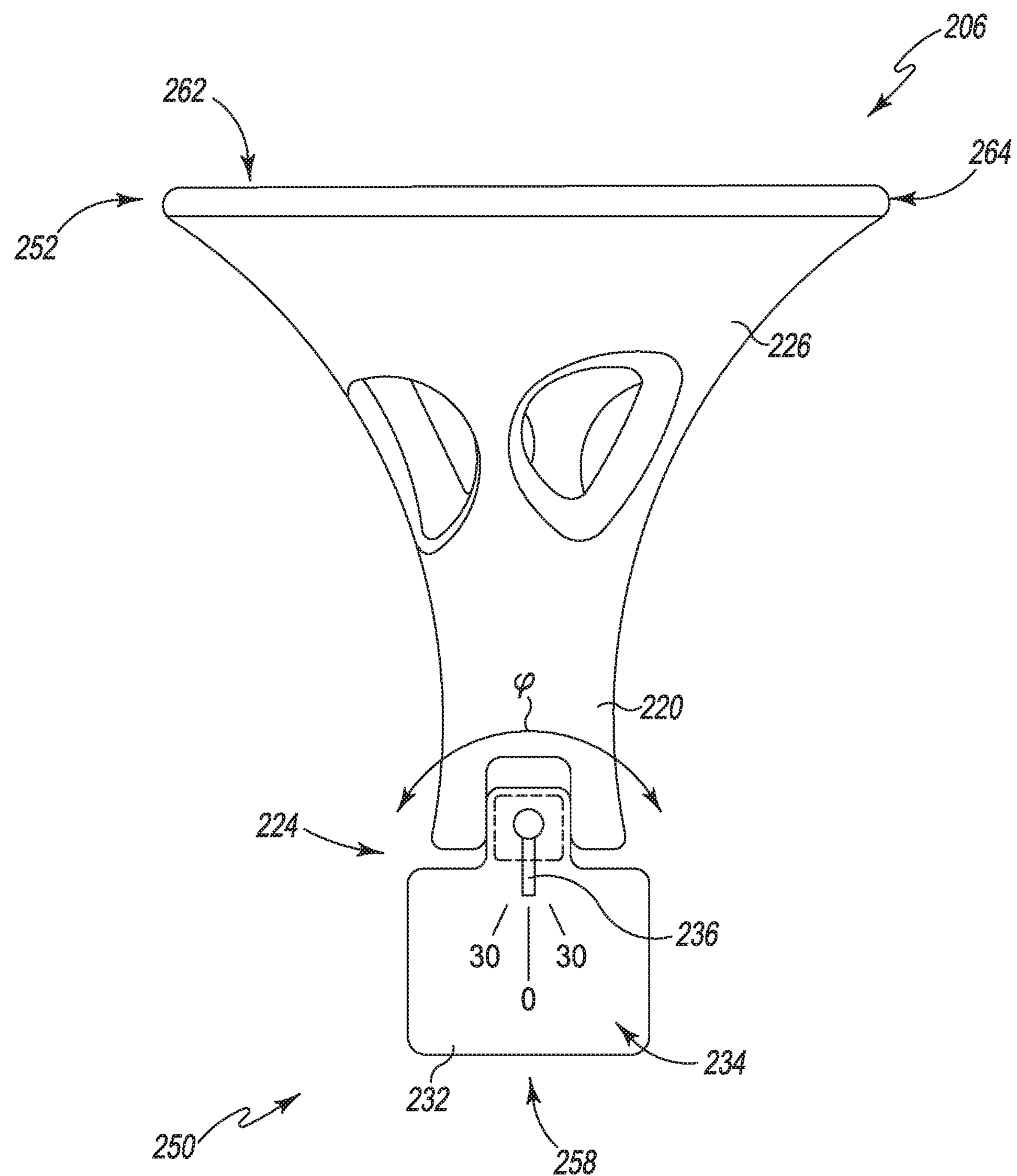
FIG. 9 is another side view of the alignment guide of FIG. 8.

Referring now to FIGS. 8-9, an embodiment of an alignment guide instrument 206 is shown. Similar to the alignment guide instrument 106, the alignment guide instrument 206 includes a body 220 that extends from a distal end 250 to a proximal end 252. The distal end 250 is configured to connect to the post 126 of the femoral broach 104, and the proximal end 252 is configured to connect to the distal rim 136 of the cup component 102. The body 220 has a length l defined from the distal end 250 to the proximal end 252.

The body 220 includes a connector block 222 located at the distal end 250 and a connector flange 226 located at the proximal end 262. The connector block 222 defines a passageway 258 that extends into the connector block 222. The passageway 258 is sized to be positioned over the post 126 of the femoral broach 104. In some embodiments, the passageway 258 may establish a friction fit on the post 126 sufficient to provide rotational stability. In some embodiments, the connector block 222 may include one or more annular tabs extending into the passageway 258 (not shown) that engage the slot 132 of the post 126 to secure the alignment guide instrument 206 to the post 126.

The connector flange 226 includes a planar rim 262 configured to engage the cup component 102. Illustratively, the planar rim 262 includes an outer circumference 264. The outer circumference 264 is sized to be received within the annular inner surface 140 of the cup component 102. The outer circumference 264 may establish a friction fit with the annular inner surface 140. In some embodiments, the connector flange 226 may further include multiple keys (not shown) that extend outwardly from the outer circumference 264 and are positioned around the outer circumference 264 of the planar rim 262. The keys may be received by the slots 146 of the cup component 102. When the alignment guide instrument 206 and the cup component 102 are connected, the planar rim 262 of the alignment guide instrument 206 and the distal rim 136 of the cup component 102 are coplanar or otherwise parallel.

The alignment guide instrument 206 further includes a universal joint 224 that connects the connector block 222 and the connector flange 226. The universal joint 224 allows the connector block 222 and the connector flange 226 to be freely rotated according to an angle θ as shown in FIG. 8 and an angle φ as shown in FIG. 9. The connector block 222 includes a side 228 that includes an angular scale 230, shown in FIG. 8. Similarly, the connector block 222 further includes a side 232 that includes an angular scale 234, shown in FIG. 9. A user may determine the current angles θ, φ of the connector block 222 relative to the connector flange 226 by referring to the angular scales 230, 234. In some embodiments, one or more of the current angles θ, φ may be read using a corresponding indicator 236 as shown in FIG. 9.

In use, similar to the alignment guide instrument 106, a surgeon may utilize the alignment guide instrument 206 to trial and install a prosthetic hip joint. The surgeon prepares the patient's femur and acetabulum as described above. With the femoral broach 104 seated in the femoral canal, the surgeon slides the alignment guide instrument 206 onto the post 126 until the distal end 250 contacts the planar surface 124. The surgeon may rotate the alignment guide instrument 206 on the post 126 until the alignment guide instrument 206 is in a predetermined orientation. Next, the surgeon connects the acetabular cup component 102 to the proximal end 252 of the alignment guide instrument 206. After being connected, the surgeon may adjust the orientation and/or position of the acetabular cup component 102 relative to the femoral broach 104 by rotating the connector flange 226 about the universal joint 224 of the alignment guide instrument 206 in the direction of the angle θ and/or the angle φ. Note that unlike the alignment guide instrument 106, the alignment guide instrument 206 does not rigidly support the acetabular cup component 102 in a predetermined position and/or orientation relative to the femoral broach 104. Rather, with the alignment guide instrument 206, the surgeon may use feedback from the angular scales 230, 234 to place the acetabular cup component 102 and the femoral broach 104 in a desired orientation. Thus, the surgeon may adjust the angles θ, φ of the alignment guide instrument 206 to achieve a desired abduction, anteversion, and/or flexion angle for the joint.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A system for use during an orthopaedic surgical procedure, the system comprising:

a femoral broach including (i) an elongated body extending along a longitudinal axis from a superior end to an inferior tip, wherein the superior end of the elongated body includes a planar outer surface and (ii) a post extending superiorly from the planar outer surface of the elongated body to a proximal tip, and an acetabular alignment guide instrument including a distal end configured to be coupled to the post of the femoral broach and a proximal engagement rim configured to be coupled to an acetabular cup component, wherein while the acetabular alignment guide instrument is coupled to the femoral broach:

the planar outer surface of the elongated body of the femoral broach defines a first imaginary plane;

the proximal engagement rim of the alignment guide instrument defines a second imaginary plane that is not parallel to the first imaginary plane;

a first angle is defined between the first imaginary plane and the second imaginary plane when the acetabular alignment guide instrument and the femoral broach are viewed in a first visual plane, wherein the first visual plane contains the longitudinal axis and an imaginary axis that extends along a topmost surface of the proximal tip of the post;

a second angle is defined between the first imaginary plane and the second imaginary plane when the acetabular alignment guide instrument and the femoral broach are viewed in a second visual plane extending orthogonal to the first visual plane and orthogonal to the planar outer surface of the elongated body; and the first angle or the second angle is nonzero;

wherein each of the first angle and the second angle has a magnitude, and when the guide instrument is coupled to the acetabular cup component, the magnitudes of the first angle and the second angle orient the acetabular cup component insertion into a patient's acetabulum at a predetermined anteversion angle and a predetermined abduction angle.

2. The system of claim 1, wherein the guide instrument further comprises an adjustment mechanism operable to change a magnitude of at least one of the first angle and the second angle.

3. The system of claim 1, wherein the proximal engagement rim of the guide instrument is configured to engage a rim of the acetabular cup component.

4. The system of claim 1, wherein the guide instrument comprises a stem including the distal end of the guide instrument and a connector flange coupled to the stem, the connector flange including the proximal engagement rim of the guide instrument.

5. The system of claim 4, wherein the proximal engagement rim includes a planar proximal rim surface, and the connector flange includes a curved inner surface that extends inwardly from the planar rim surface to define a proximal chamber in the guide instrument.

6. The system of claim 5, wherein:

the stem includes a passageway that extends inwardly from the distal end of the guide instrument and opens into the proximal chamber of the guide instrument, the passageway being sized to receive the post of the femoral broach.

7. The system of claim 1, wherein the femoral broach includes a plurality of cutting teeth defined along an outer surface of the elongated body.

8. A system for use during an orthopaedic surgical procedure, the system comprising:

a femoral broach including (i) an elongated body extending along a longitudinal axis from a superior end to an inferior tip, wherein the superior end of the elongated body includes a planar outer surface and (ii) a post extending superiorly from the planar outer surface of the elongated body to a proximal tip, and an acetabular alignment guide instrument including a distal end configured to be coupled to the post of the femoral broach and a proximal end configured to be coupled to an acetabular cup component, the proximal end including a proximal engagement rim, wherein while the guide instrument is coupled to the femoral broach, the guide instrument is sized to orient the proximal engagement rim relative to the femoral broach such that:

(i) a first angle is defined between a first imaginary plane extending along the planar outer surface of the elongated body of the femoral broach and a second imaginary plane extending along the proximal engagement rim when the guide instrument and the femoral broach are viewed in a first visual plane, wherein the first visual plane contains the longitudinal axis and an imaginary axis that extends along a topmost surface of the proximal tip of the post, and (ii) a second angle is defined between the first imaginary plane and the second imaginary plane when the guide instrument and the femoral broach are viewed in a second visual plane, the second visual plane extending orthogonal to the first visual plane and orthogonal to the planar outer surface of the elongated body, wherein the first angle or the second angle are nonzero;

wherein the guide instrument further comprises an adjustment mechanism operable to change a magnitude of at least one of the first angle and the second angle.

9. The system of claim 8, wherein the guide instrument comprises a stem including the distal end of the guide instrument and a connector flange coupled to the stem, the connector flange including the proximal end of the guide instrument and being configured to engage the rim of the acetabular cup component.

10. The system of claim 9, wherein the connector flange includes an engagement surface configured to engage the inner surface of the acetabular cup component.

11. The system of claim 10, wherein the engagement surface is a planar rim surface, and the connector flange includes a curved inner surface that extends inwardly from the planar rim surface to define a proximal chamber in the guide instrument.

12. The system of claim 9, wherein the stem of the guide instrument is sized to be positioned over the post.

13. The system of claim 8, wherein the guide instrument comprises a proximal end configured to be coupled to at least one of an acetabular prosthetic cup component or an acetabular cup trial instrument corresponding to the acetabular prosthetic cup component.

* * * * *